US00PP19365P2

(12) United States Plant Patent
Zaiger et al.

(10) Patent No.: US PP19,365 P2
(45) Date of Patent: Oct. 21, 2008

(54) CHERRY TREE NAMED 'ROYAL EDIE'

(50) Latin Name: *Prunus avium*
Varietal Denomination: Royal Edie

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/008,668

(22) Filed: Jan. 14, 2008

(51) Int. Cl.
*A01H 5/00* (2006.01)

(52) U.S. Cl. ..... Plt./181

(58) Field of Classification Search ..... Plt./181
See application file for complete search history.

*Primary Examiner*—Annette H Para

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit maturing in late maturity season.
2. Fruit with attractive red skin color.
3. Fruit with very good flavor and eating quality.
4. Heavy and regular production of large size fruit.
5. Vigorous, upright growth of tree.

1 Drawing Sheet

Botanical classification: *Prunus avium.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecific are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Bing' Cherry (non-patented) and 'Royal Dawn' Cherry (U.S. Plant Pat. No. 13,131).

ORIGIN OF THE VARIETY

The present new variety of cherry tree (*Prunus avium*) was developed by us in our experimental orchard located near Modesto, Calif. The new cherry tree originated from an open pollinated proprietary seedling selection with the field identification number '92LB341'. The seed parent (92LB341) originated as a cross between a proprietary selected seedling from an open pollinated 'Bing' Cherry (non-patented) and 'Royal Dawn' Cherry (U.S. Plant Pat. No. 13,131). A large number of these open pollinated seedlings were budded on established trees of 'Mahaleb' Rootstock (non-patented) to accelerate fruit production. Under close and careful observation the present seedling exhibited desirable fruit and tree characteristics and was selected in 1998 for asexual propagation and commercialization.

ASEXUAL REPRODUCTION OF THE VARIETY

Additional asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of cherry tree is of large size, vigorous upright growth and a productive and regular bearer of large size fruit with good firmness, very good flavor and eating quality. The fruit is further characterized by having an attractive red skin color and maturing in the late season. The new variety is an excellent pollinator for our proprietary selection '25Z1046' that matures close to the same time and is similar in appearance, which facilitates the economics of harvesting the fruit together. In comparison to its ancestor 'Bing' Cherry (non-patented) the fruit of the new variety is larger in size and is approximately 10 days later in maturity. In comparison to 'Royal Dawn' Cherry (U.S. Plant Pat. No. 13,131) the fruit of the new variety matures approximately 24 days later and is larger in size. In comparison to its immediate seed parent (92LB341) the fruit is larger in size and is approximately 10 days later in maturity.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in the place. The photographic illustration was taken shortly after being picked (shipping ripe) from a 13 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of a 13 year old specimen grown near Modesto, Calif., with color in accordance with Munsell Book of Color.

Tree:

*Size.*—Large. Tree pruned to 3 to 4 meters in height and width for economical harvesting of fruit.

*Vigor.*—Vigorous, tree growth reaching 1 to 2 meters the first growing season. Growth rate varies with soil type and depth, cultural practices and climatic conditions.

*Form.*—Upright. During the first and second growing seasons scaffolds are selected and tied down to increase crotch angle and help spread tree to desired width of 3 to 4 meters.

*Branching habit.*—Upright, crotch angle approximately 25° when juvenile, the weight of the fruit tends to increase branch angles.

*Productivity.*—Productive. Produces adequate fruit set annually.

*Bearer.*—Regular, adequate fruit set nine consecutive years.

*Fertility.*—Self sterile, pollinator required.

*Density.*—Medium dense. Normally pruned to vase shape to allow more sunlight in center of tree to enhance health of fruit spurs and fruit color.

*Hardiness.*—Hardy in all stone fruit growing areas of California. Tree grown in USDA Hardiness Zone 9. Winter chilling requirement is approximately 750 hours at or below 45° F.

Trunk:

*Size.*—Large. Measured 78.7 cm at 53.3 cm above ground on a 13 year old tree. Varies with soil type, climatic conditions and cultural practices.

*Stocky.*—Medium stocky.

*Texture.*—Medium rough, roughness increases with age of tree.

*Color.*—Varies from 5YR 2/4 to 7.5YR 3/2.

Branches:

*Size.*—Medium. Average circumference 21.3 cm at 1.2 meters above ground.

*Surface texture.*—Smooth on new growth becoming medium rough on mature growth.

*Lenticels.*—Average number 13 in a 25.8 square cm section. Average length 6.7 mm. Average width 2.4 mm. Color varies from 5YR 6/10 to 7.5YR 5/8.

*Color.*—New growth varies from 5Y 5/4 to 5Y 6/4. Old growth varies from 5YR 2/4 to 7.5YR 6/2, varies with age of growth.

Leaves:

*Size.*—Large. Average length 142.6 mm. Average width 65.6 mm.

*Form.*—Varies from elliptic to lanceolate.

*Apex.*—Acuminate.

*Base.*—Cuneate.

*Margin.*—Serrate.

*Thickness.*—Medium.

*Surface texture.*—Upper surface relatively smooth, slight indentation over leaf veins, glabrous. Lower surface relatively smooth, slight ridges created by midrib and pinnate venation, glabrous.

*Petiole.*—Average length 38.5 mm. Average width 2.2 mm. Longitudinally grooved. Color varies from 2.5GY 6/4 to 2.5GY 6/6. Glabrous.

*Glands.*—Reniform. Average length 3.1 mm. Average width 2.0 mm. Number varies from 1 to 3, average number 3. Located primarily on the upper portion of petiole. Color varies from 7.5Y 7/6 to 5Y 5/4. Where exposed to the sun color varies from 5R 3/8 to 5R 3/10.

*Color.*—Upper surface varies from 5GY 4/4 to 5GY 3/6. Lower surface varies from 2.5GY 6/4 to 2.5GY 5/4. Midvein color varies from 10Y 8/4 to 2.5GY 8/4.

Flower buds:

*Size.*—Large. Average length 18.4 mm. Average diameter 9.9 mm.

*Hardiness.*—Hardy with respect to California winters.

*Form.*—Plump, conical.

*Pedicel.*—Average length 17.4 mm. Average width 1.1 mm. Color varies from 2.5GY 5/6 to 5GY 5/6.

*Color.*—N 9.5/ (white). Some buds have 2.5R 5/8 on upper edges of petals. Color fades to white as buds open.

*Number of buds per spur.*—Average number 7, varies from 3 to 9.

Flowers:

*size.*—Large. Average height 20.6 mm. Average diameter 36.4 mm.

*Petals.*—Number 5, alternately arranged to sepals. Nearly orbicular, narrows at point of attachment. Margin is sinuate with a slight cleft at the apex of some petals. Color N 9.5/ (white). Average length 18.8 mm. Average width 18.3 mm.

*Sepals.*—Number 5, alternately arranged to petals. Triangular shape. Average length 7.7 mm. Average width 5.6 mm. Both upper and lower surfaces glabrous. Margin entire. Color — upper surface varies from 5GY 6/6 to 5GY 6/8. Lower surface varies from 5GY 5/6 to 5GY 4/6 with 5R 3/6 on some areas.

*Stamens.*—Average number per flower 33. Average filament length 11.8 mm. Filament color N 9.5/ (white). Anther color varies from 5Y 8/8 to 5Y 8/10.

*Pollen.*—Self sterile, pollinator required. Color varies from 5Y 7/10 to 5Y 7/12.

*Pistil.*—Normally 1 per flower. Average length 15.4 mm. Position of stigma is an average of 1.0 mm below the anthers. Surface — glabrous. Color varies from 2.5GY 7/6 to 2.5GY 6/6.

*Fragrance.*—Very slight.

*Blooming period.*—Date of First Bloom Mar. 13, 2007. Date of Petal Fall Mar. 24, 2007, varies slightly with climatic conditions.

*Color.*—N 9.5/ (white).

*Number flowers per flower bud.*—Average 4, varies from 2 to 5.

*Pedicel.*—Average length 19.2 mm. Average width 1.2 mm. Color varies from 2.5GY 5/8 to 5GY 5/8.

Fruit:

*Maturity when described.*—Firm ripe.

*Date of first picking.*—Jun. 4, 2007.

*Date of last picking.*—Jun. 11, 2007, varies slightly with climatic conditions.

*Size.*—Large. Average diameter axially 26.6 mm. Average transversely in suture plane 31.7 mm. Average weight 14.2 grams. Average weight varies slightly with fertility of the soil, amount of thinning and climatic conditions.

*Form.*—Globose, slightly flattened at apex and base.

*Suture.*—Nearly smooth, extends from base to apex.

*Ventral surface.*—Nearly smooth to very slightly lipped.

*Apex.*—Varies from slightly retuse to rounded.

*Base.*—Varies from flat to slightly retuse.

*Cavity.*—Rounded. Average depth 3.4 mm. Average diameter 8.8 mm.

*Stem.*—Large. Average length 47.0 mm. Average diameter 1.2 mm. Color varies from 2.5GY 6/4 to 5GY 5/4.

Flesh:

*Ripens.*—Evenly.

*Texture.*—Very firm.

*Fibers.*—Few, small and tender.

*Firmness.*—Very firm, comparable to 'Royal Dawn' Cherry (U.S. Plant Pat. No. 13,131).

*Aroma.*—Moderate.

*Amydgalin.*—Undetected.

*Eating quality.*—Very good.

*Flavor.*—Very good, good balance between acid and sugar.

*Juice.*—Moderate amount, enhances flavor.

*Brix.*—Average Brix 18.6°, varies slightly with amount of fruit per tree and climatic conditions.

*Color.*—Varies from 2.5R 3/10 to 5R 4/8. Pit cavity varies from 2.5R 2/8 to 5R 2/8.

Skin:

*Thickness.*—Medium.

*Surface.*—Smooth.

*Bloom.*—Wanting.

*Tendency to crack.*—None during dry weather. Only slight tendency to crack in wet weather, varies with stage of fruit maturity.

*Color.*—Varies from 5R 3/6 to 5R 2/6.

*Tenacity.*—Tenacious to flesh.

*Astringency.*—None.

Stone:

*Type.*—Semi-cling.

*Size.*—Large. Average length 10.9 mm. Average width 10.0 mm. Average thickness 8.0 mm.

*Form.*—Ovoid.

*Base.*—Flat.

*Apex.*—Slightly pointed. Average length 0.1 mm.

*Surface.*—Smooth except for small ridges near the suture.

*Sides.*—Equal to unequal. Some stones have one side extending further from the suture plane.

*Ridges.*—A small, narrow ridge on each side of the suture, extends from base to apex.

*Tendency to split.*—None.

*Color.*—Varies from 10YR 7/6 to 2.5Y 8/6 when dry.

Kernel

*Form.*—Ovoid.

*Taste.*—Bitter.

*Viability.*—Viable, good embryo development.

*Size.*—Large. Average length 8.0 mm. Average width 6.2 mm. Average depth 5.7 mm.

*Skin.*—Color varies from 5Y 9/2 to 7.5Y 9/2 when dry.

Use: Dessert.

*Market.*—Local and long distance.

Keeping quality: Good, held well for 14 days in cold storage at 38° to 42° F. and maintained good appearance and eating quality.

Shipping quality: Good, showed minimal bruising or scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect, susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of cherry tree, substantially as illustrated and described, characterized by its large size, vigorous, upright growth and being a regular and productive bearer or large size fruit, that have an attractive red skin color; the fruit is further characterized by its very good flavor and eating quality, with good handling and shipping ability, and in comparison to 'Bing' Cherry (non-patented) the fruit of the new variety is larger in size and is approximately 10 days later in maturity.

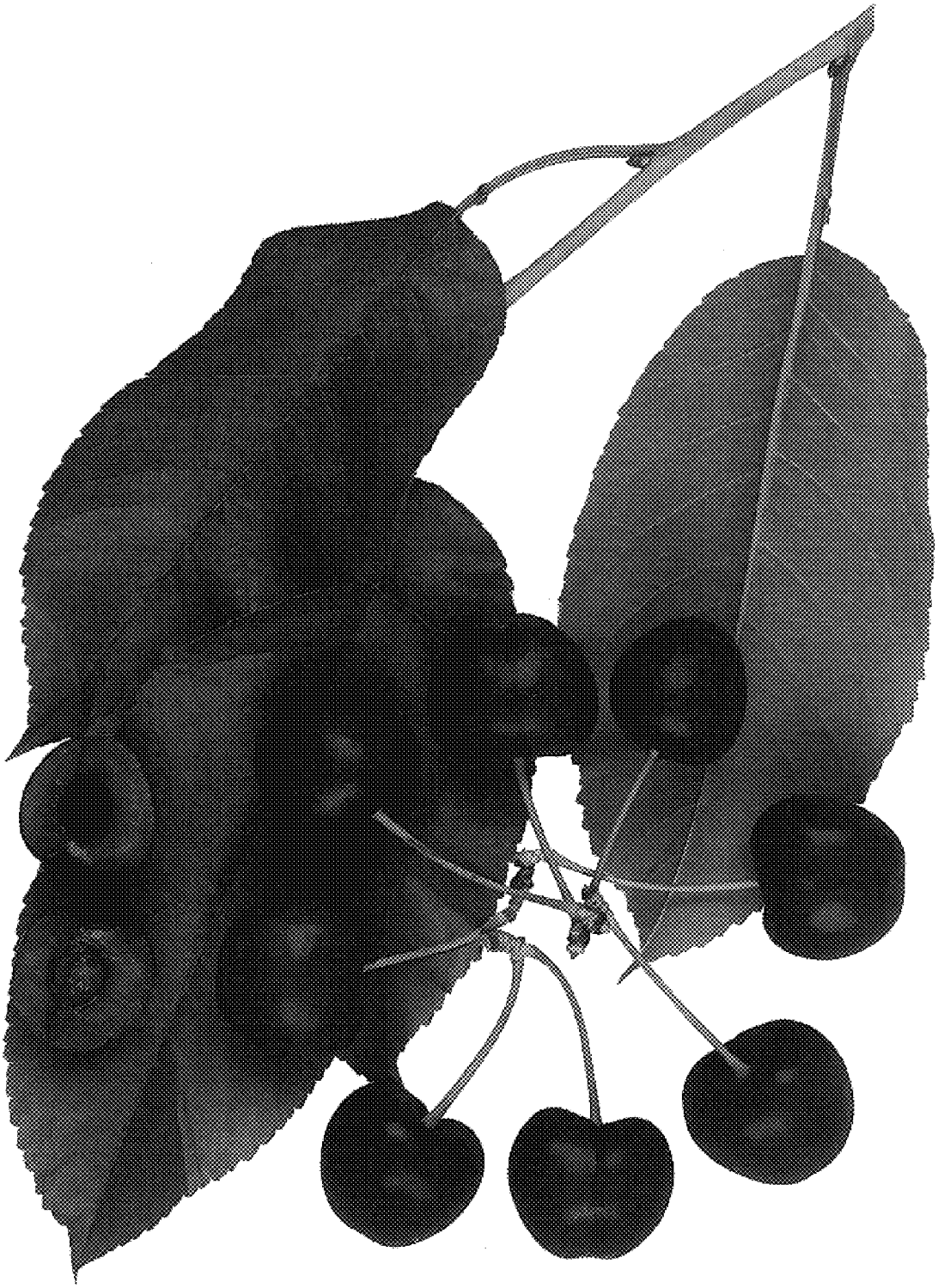

* * * * *